US012773505B2

(12) United States Patent
Lee et al.

(10) Patent No.: US 12,773,505 B2
(45) Date of Patent: Oct. 27, 2026

(54) INHALER TESTING APPARATUS AND METHOD

(71) Applicant: Logan Instruments Corporation, Somerset, NJ (US)

(72) Inventors: Luke Lee, Belle Mead, NJ (US); Seth Michael Endy, Whitehouse Station, NJ (US)

(73) Assignee: Logan Instruments Corporation, Somerset, NJ (US)

( * ) Notice: Subject to any disclaimer, the term of this patent is extended or adjusted under 35 U.S.C. 154(b) by 299 days.

(21) Appl. No.: 18/487,195

(22) Filed: Oct. 16, 2023

(65) Prior Publication Data

US 2024/0165349 A1 May 23, 2024

Related U.S. Application Data

(60) Provisional application No. 63/379,566, filed on Oct. 14, 2022.

(51) Int. Cl.
*A61M 15/00* (2006.01)

(52) U.S. Cl.
CPC .... *A61M 15/0005* (2014.02); *A61M 15/0021* (2014.02); *A61M 15/0066* (2014.02); *A61M 2205/33* (2013.01)

(58) Field of Classification Search
CPC .......... A61M 15/0005; A61M 15/0021; A61M 15/0066; A61M 2205/33; A61M 15/009; A61M 11/00; A61M 2205/103; A61M 2205/106; A61M 2205/70
See application file for complete search history.

(56) References Cited

U.S. PATENT DOCUMENTS

| | | | |
|---|---|---|---|
| 6,520,673 | B2 | 2/2003 | Marple et al. |
| 8,197,120 | B2 | 6/2012 | Westmoreland et al. |
| 10,451,459 | B2 | 10/2019 | Copley et al. |
| 10,993,881 | B1 | 5/2021 | Karpman et al. |

(Continued)

FOREIGN PATENT DOCUMENTS

| | | | |
|---|---|---|---|
| CA | 3049504 | A1 | 7/2018 |
| CN | 212846808 | U | 3/2021 |

(Continued)

OTHER PUBLICATIONS

Machine Translation of CN-116929734-A (Year: 2023).*
International Search Report and Written Opinion for PCT/US2023/076865 issued Mar. 18, 2024.

*Primary Examiner* — Stephen D Meier
*Assistant Examiner* — Quang X Nguyen
(74) *Attorney, Agent, or Firm* — Brian Roffe

(57) ABSTRACT

Inhaler testing apparatus includes a frame, a rotatable carousel rotatably mounted on said frame and that support tubes each having a closed end and an open end, an inhaler retaining apparatus on said frame that retains an inhaler being tested, and actuating mechanisms on the frame for moving the inhaler retaining apparatus in two directions, for shaking and actuating the inhaler being tested. A control unit controls rotation of the carousel and the actuating mechanisms to move the carousal relative to the inhaler being tested to cause controlled shaking of the inhaler and delivery of material from the inhaler into each tube. Analysis of the material in the tubes constitutes a test of the inhaler.

14 Claims, 9 Drawing Sheets

(56) References Cited

U.S. PATENT DOCUMENTS

| | | | |
|---|---|---|---|
| 2004/0261792 A1 | 12/2004 | Wolf et al. | |
| 2008/0047372 A1 | 2/2008 | Bridge et al. | |
| 2008/0316857 A1 | 12/2008 | Westmoreland et al. | |
| 2016/0302484 A1 | 10/2016 | Gupta et al. | |
| 2023/0321370 A1* | 10/2023 | Farina | A61M 15/0065 73/118.01 |

FOREIGN PATENT DOCUMENTS

| | | | | |
|---|---|---|---|---|
| CN | 112891731 A | | 6/2021 | |
| CN | 116929734 A | * | 10/2023 | G01M 13/00 |
| GB | 2371861 A | | 8/2002 | |
| WO | 0128615 A2 | | 4/2001 | |
| WO | 03055539 A2 | | 7/2003 | |
| WO | 2006097747 A1 | | 9/2006 | |

* cited by examiner

INHALER TESTING APPARATUS AND METHOD

CROSS-REFERENCE TO RELATED APPLICATION

This application claims priority of U.S. patent application Ser. No. 63/379,566 filed Oct. 14, 2022, the disclosure of which is incorporated by reference herein.

FIELD OF THE INVENTION

The present invention is generally directed to an apparatus and method for testing a metered dose inhaler unit or inhaler, and more particularly, to an apparatus and method for automating the testing process.

The present invention is also directed to equipment used with an inhaler testing apparatus, such as an inhaler shaking apparatus that shakes the inhaler prior to the test, and a washing device that washes tubes used in the test.

BACKGROUND OF THE INVENTION

Medicinal drug formulations useful in inhalation therapy for treating respiratory disorders, such as asthma, are frequently administered to patients orally or nasally in metered, aerosolized doses. Such aerosolized drug formulations are commonly provided in the form of a suspension or emulsion consisting of a pharmaceutical compound in micronized powder form and a suspending medium such as a liquefied gas or propellant. The suspension is initially stored within a sealed canister capable of withstanding the pressure required to maintain the propellant as a liquid. The suspension can then be dispensed in metered, aerosolized doses from the canister upon actuation of an atomized material delivery device such as a metered dose inhaler (MDI) unit. A variety of atomized material devices are well-known in the pharmaceutical industry.

Patients frequently rely upon medication delivered by MDI units, commonly known as inhalers, for rapid or sustained treatment of respiratory disorders, such as asthma, which are debilitating and, in some instances, even life threatening. As a result, it is essential that the prescribed dose of aerosolized drug formulation being delivered to the patient's lungs consistently meet the specifications claimed by the manufacturer and comply with stringent requirements set forth by drug regulator authorities, such as the Food and Drug Administration (FDA). Therefore, testing of inhalers for effective and efficient drug delivery is a necessary part of a manufacturer's quality assurance procedure.

One aspect of the testing of inhalers for effective and efficient drug delivery involves measuring or characterizing the aerodynamic particle size of atomized medicament, which is released upon actuation of a valve assembly. If the aerodynamic particle size of atomized medicament is too large, medicament will be deposited on the inside surface of the patient's throat. As a result, the prescribed dose of respiratory medicament is prevented from reaching the patient's lungs, thereby thwarting the patient from receiving the benefit of the potentially life-saving therapeutic effects of medicament. If, on the other hand, the aerodynamic particle size of atomized medicament is too small, medicament will not be adequately transferred to the patient's lungs. As a result, the prescribed dose of respiratory medicament is simply exhaled by the patient without having exhibited any substantial therapeutic effect.

OBJECTS AND SUMMARY OF THE INVENTION

It is an object of at least one embodiment of the present invention to provide apparatus and method for testing metered dose inhaler units or inhalers to determine operating characteristics and compliance with requirements therefor and/or for automating the process for testing a metered dose inhaler unit.

In order to achieve one or both of these objects or others, an inhaler testing apparatus in accordance with the invention includes a frame, a rotatable carousel rotatably mounted on the frame and configured to support a plurality of tubes each having a closed end and an open end, an inhaler retaining apparatus on the frame and configured to retain an inhaler, and various actuating mechanisms to move the inhaler retaining apparatus along a first axis (e.g., vertically), to shake the inhaler when retained by the inhaler retaining apparatus and move the inhaler retaining apparatus along a second axis (horizontally toward the carousel), and to actuate the inhaler when present on the inhaler retaining apparatus. For testing, a control unit on the frame controls the carousel, and the actuating mechanisms to rotate the carousal relative to the inhaler retained by the inhaler retaining apparatus to cause controlled shaking of the inhaler and delivery of material from the inhaler into each tube retained by the carousel. Analysis of the material in the tubes constitutes a test of the inhaler.

Typically, in view of the limited number of tubes and the test parameters, specific doses of a total amount of doses provided by the inhaler are selected for testing and other doses wasted.

Other and further objects, advantages and features of the present invention will be understood by reference to the following specification in conjunction with the annexed drawings.

BRIEF DESCRIPTION OF THE DRAWINGS

The invention, together with further objects and advantages thereof, may best be understood by reference to the following description taken in conjunction with the accompanying drawings wherein like reference numerals identify like elements.

DETAILED DESCRIPTION OF THE INVENTION

Figure 1:
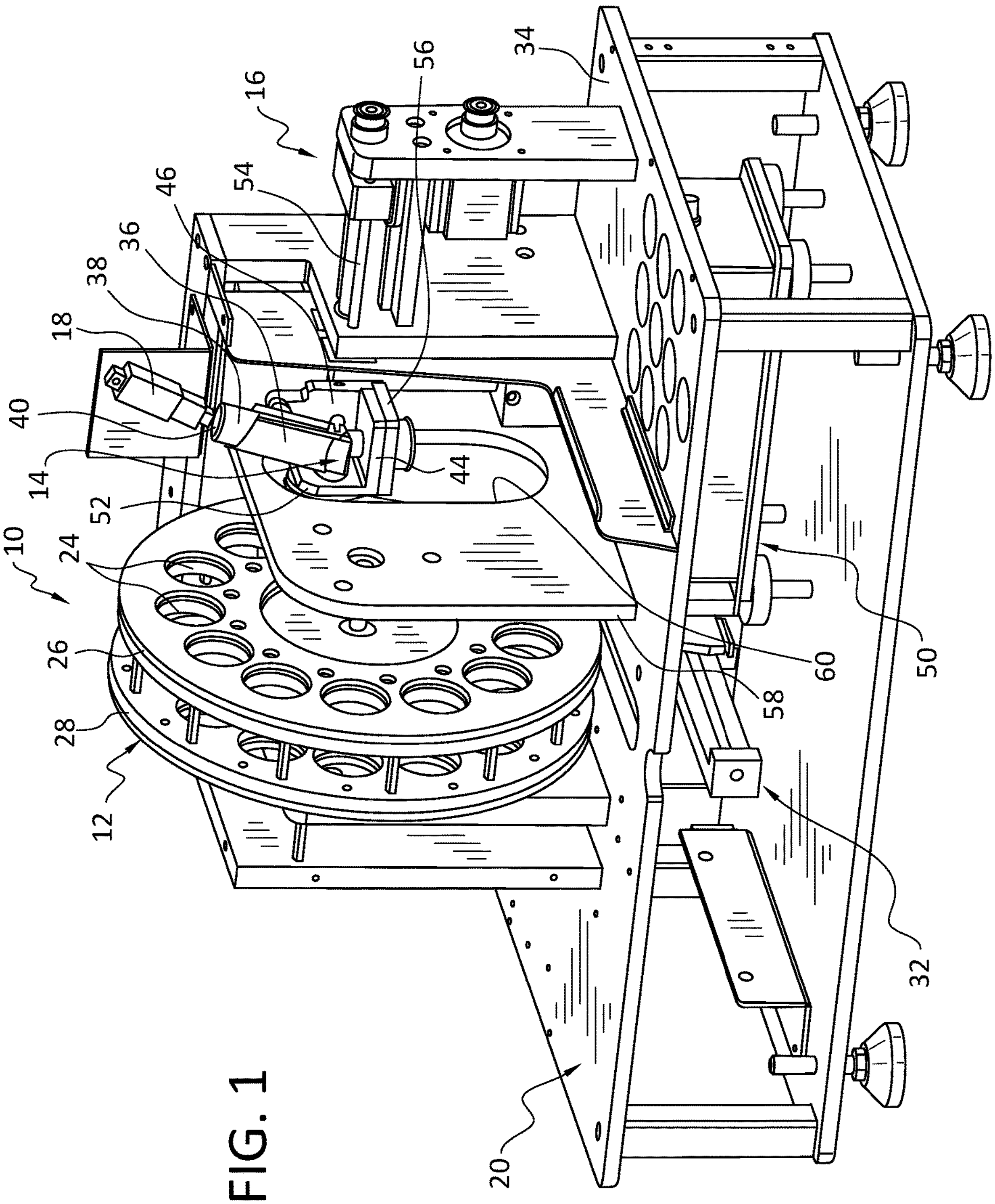
FIG. 1 is a perspective view of an apparatus of the invention used in a method of the invention.

Referring to the accompanying drawings wherein like reference numerals refer to the same or similar elements, an inhaler testing apparatus 10 in accordance with the invention includes several primary components namely a rotatable carousel 12, an inhaler retaining apparatus 14, a first actuating device 46 that moves the inhaler retaining apparatus along a first axis (vertically alongside the carousel 12 as shown), a second actuating device 16 that moves the inhaler retaining apparatus or the inhaler being tested when retained thereby along a second axis different than the first (horizontally toward the carousel 12 as shown), and a third actuating device 18 that causes actuation of the inhaler being tested when present on the inhaler retaining apparatus 14, all of which are mounted on a frame 20 (see FIG. 1). Each actuating device 16, 18 may comprise an actuator or a motor or other structure that performs the functions disclosed herein for these devices. The frame 20 is constructed to preferably rest on a flat surface such as a table and includes whatever structure is necessary to achieve this stable positioning for operation.

Figure 5:
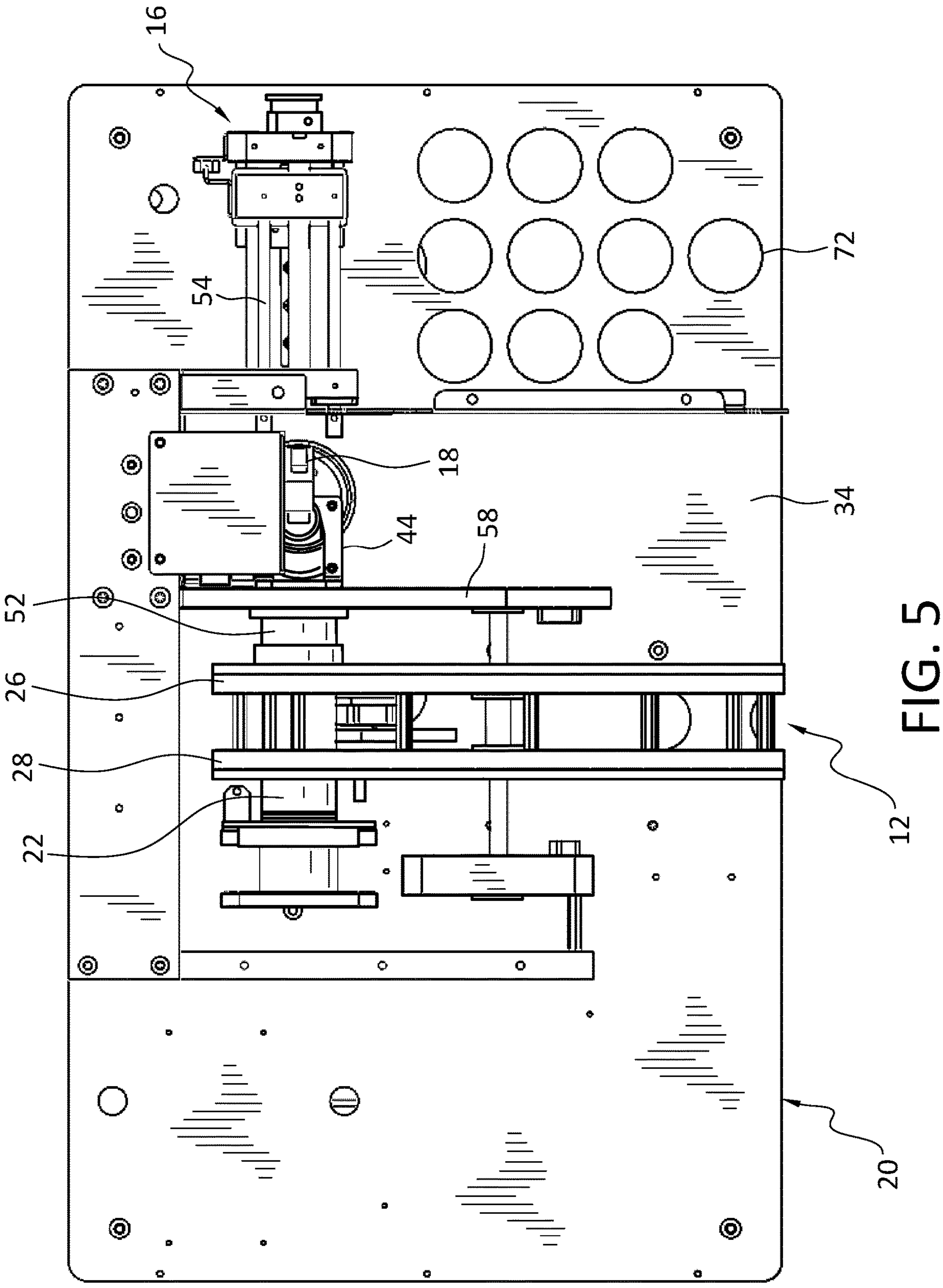
FIG. 5 is a top view of the apparatus shown in FIG. 1.
Figure 6:
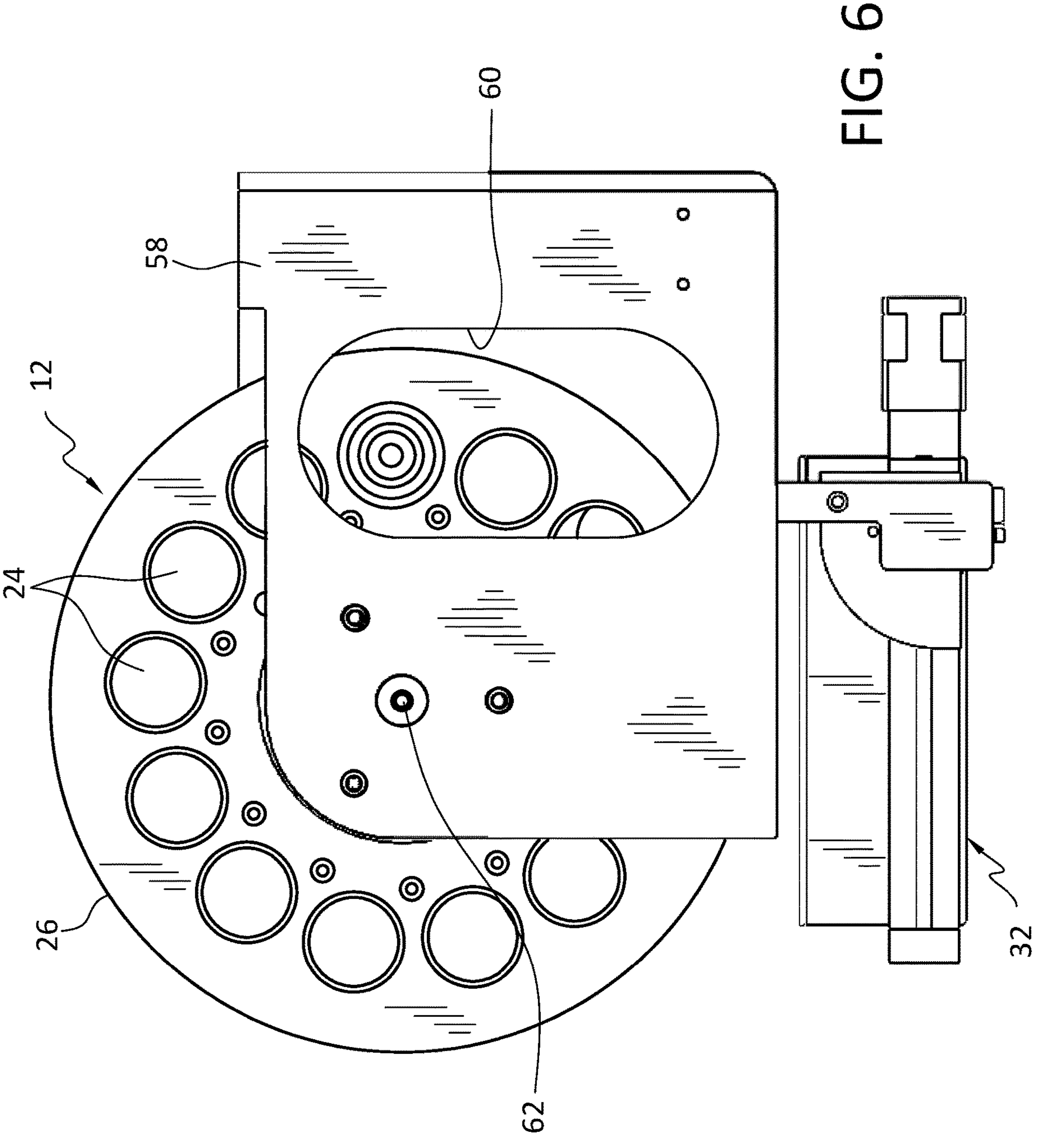
FIG. 6 is a side view of the carousel of the apparatus shown in FIG. 1.

The carousel 12 has a circular shape and is mounted to rotate about a substantially horizontal, central axis extending between lateral sides of the frame 20. Carousel 12 is configured to support a plurality of tubes 22, preferably thirteen for reasons that will be explained below (see FIGS. 4-6). Tubes 22 are containers that have an open end, i.e., an opening, and a closed end. The tubes 22 are configured to retain particulate matter sprayed into them through their opening. Tubes 22 are secured to the carousel 12 by passing them through aligning pairs of openings 24 in two separated circular plates 26, 28 of the carousel 12. Each tube 22 includes a flange 30 at or around the open end and are inserted with the rear, closed end first through the opening 24 in one circular plate 26 to rest against the front surface of this plate 26. A single plate may be used instead of two circular plates and the plates, whether one or two, may be shapes other than circular although circular is preferred since the carousel 12 is rotatable.

A rotation mechanism 32 is attached to the carousel 12 to enable the carousel 12 to rotate about its central axis. The rotation mechanism 32 includes a motor situated underneath a base 34 of the frame 20. The motor engages with the carousel 12 to push it and thereby causes its rotation. Rollers are provided on the side of the carousel 12 to guide the rotational movement of the carousel 12. Instead of the motor and rollers, other structures to cause rotation of the carousel 12 is also possible and encompassed within the scope and spirit of the invention. This structure will be considered as rotation means for engaging with and causing rotation of the carousel 12 and can be various types of structure.

Inhaler retaining apparatus 14 is configured to retain a metered dose inhaler (MDI) 36. A brief overview of a typical inhaler 36 and its manner of use is provided, especially since the manner of use is relevant to the operation of the apparatus 10.

The inhaler 36 includes a canister 38 operatively loaded into a delivery device and which has an aerosol dose metering valve assembly housed within a valve end of the canister 38. The valve assembly typically has a spring-loaded hollow valve stem, and the details of a typical valve assembly and its interaction with the valve stem are well-understood. A medicament-containing suspension is dispensed from the canister 38 by actuation of the valve assembly. Actuation is accomplished by activation of the valve stem through which a metered and substantially repeatable dose of medicament is delivered from the canister.

In order to deliver medicament to the patient with suitable efficacy, the canister operates in conjunction with a delivery device. The delivery device includes a housing having a canister cavity into which the canister 38 is operatively loaded, and a mouthpiece. A nozzle assembly is arranged within a housing of the delivery device. The nozzle assembly includes a valve stem receiving bore fluidly communicating with a nozzle orifice that is aimed toward an open end of the mouthpiece.

In preparation for its use and the testing, the canister 38 is loaded into a canister cavity of the delivery device through an open end thereof until the valve stem of the valve assembly is fitted into a valve stem-receiving bore of the nozzle assembly. An exposed end 40 of the canister 38 typically extends to some degree outside of the housing of delivery device. The patient then aims the mouthpiece towards, or places the mouthpiece into, his or her mouth and pushes with a downward force on the exposed end 40 of the canister 38. As a result, the canister 38 is displaced in a downward manner, with respect to the valve stem, thereby actuating valve assembly and causing a metered dose of medicament to be emitted from the valve stem through the nozzle orifice, and through the open end of the mouthpiece.

As the suspension is forced from the canister 38 through the valve stem by the high vapor pressure of the liquid propellant, the propellant rapidly vaporizes therefore leaving a fast moving stream of atomized particles of the medicament. This atomized medicament is directed into the mouth of the patient by the mouthpiece of the delivery device, which has previously been aimed toward, or inserted into, the patient's mouth. Owing to the design of the valve assembly, the design of the nozzle assembly, and/or the pressure differential between the interior of the canister 38 and the exterior ambient atmosphere, a short burst of precisely metered, atomized medicament is thereby delivered to the patient upon actuation. The patient simultaneously inhales medicament into his or her lungs concurrently with actuation of the valve assembly.

Figure 2:
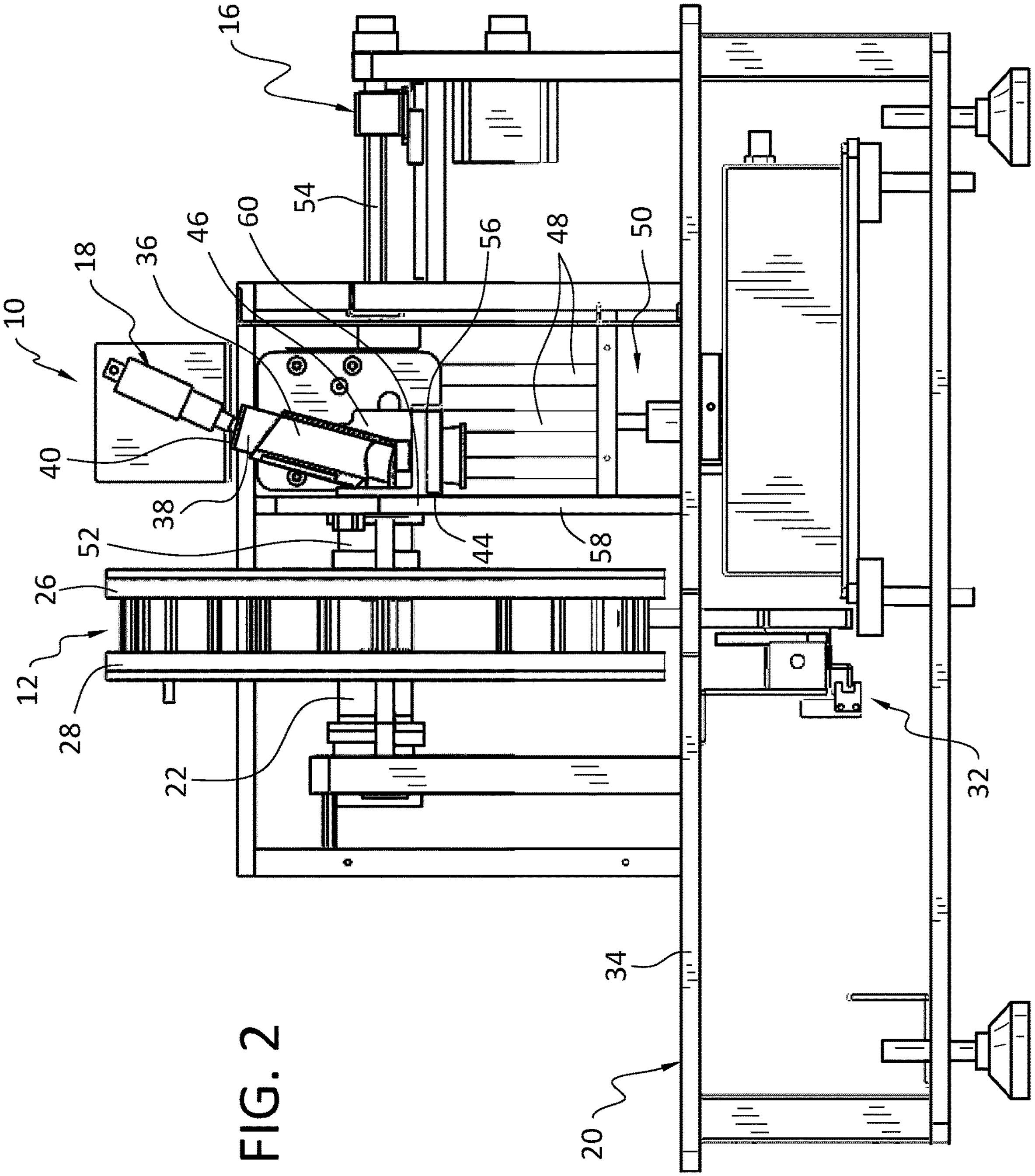
FIG. 2 is a front view of the apparatus shown in FIG. 1.
Figure 3:
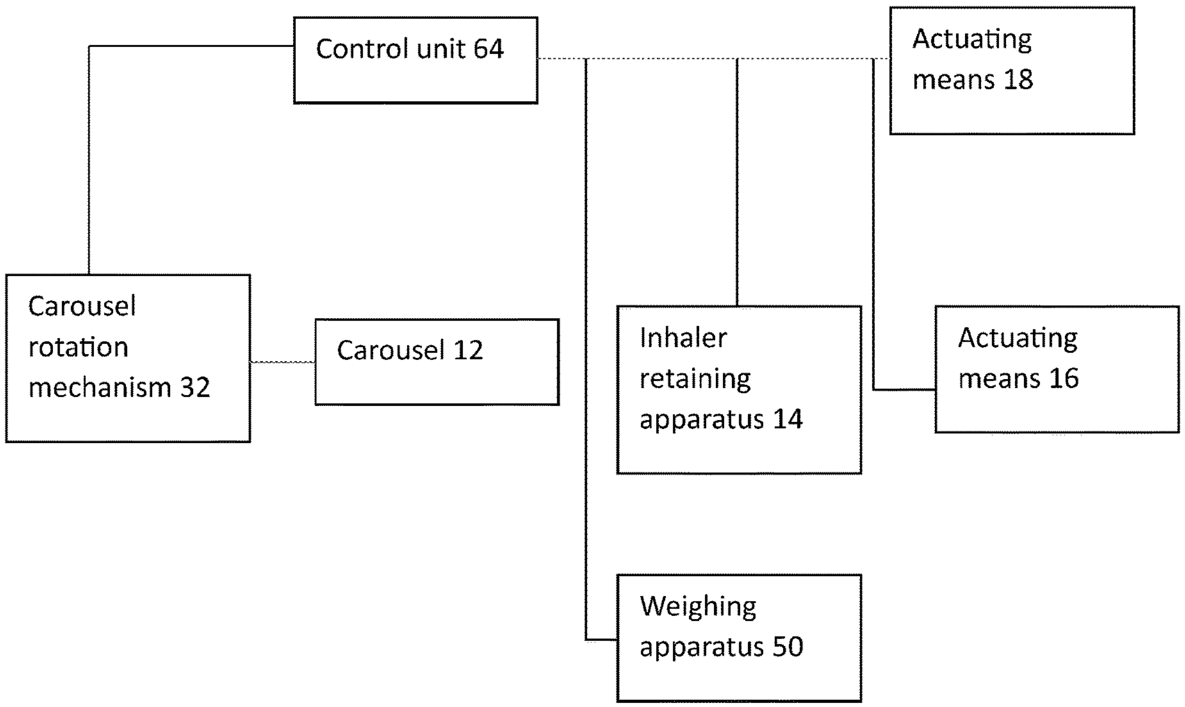
FIG. 3 is a schematic of the apparatus shown in FIG. 1.
Figure 4:
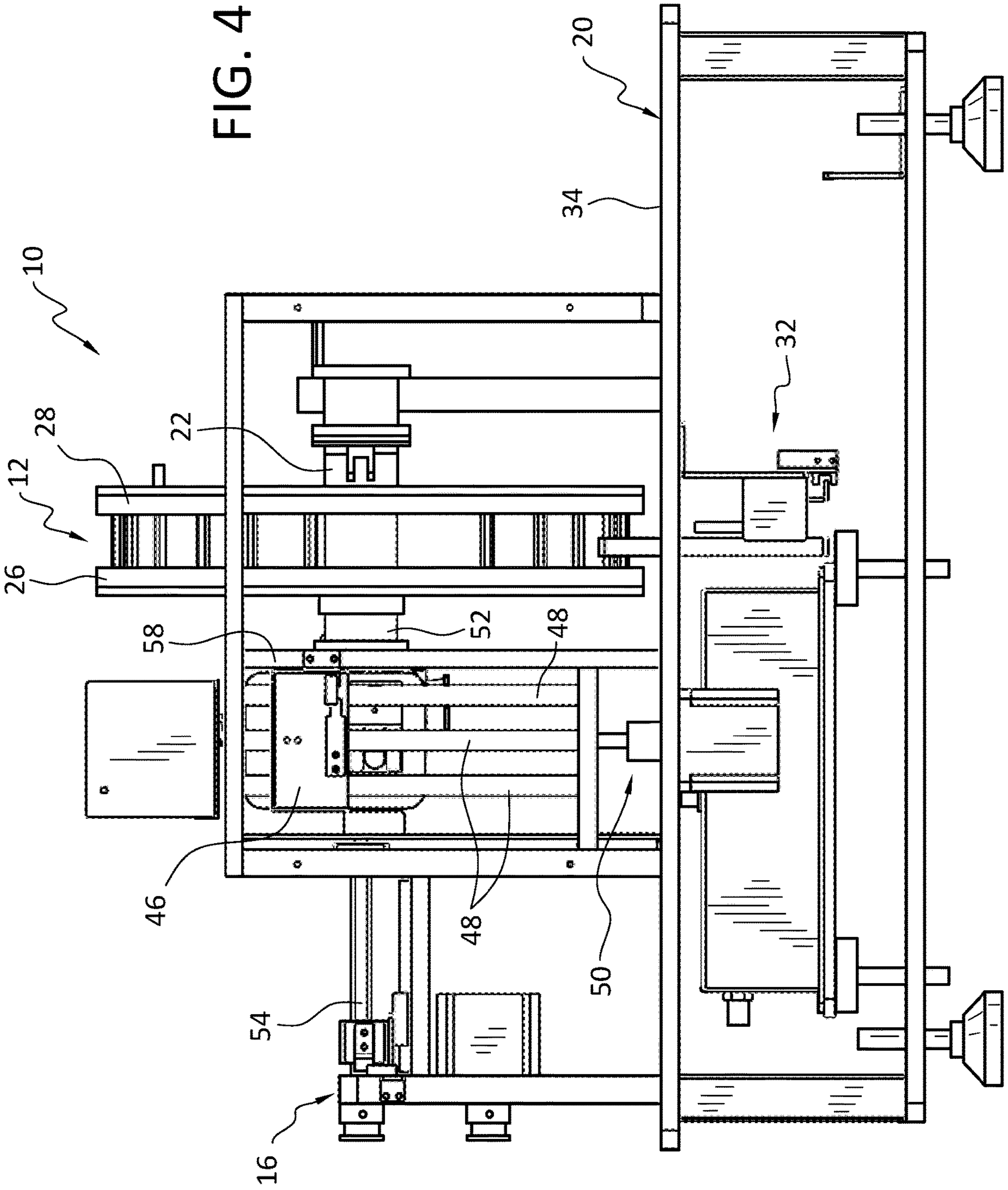
FIG. 4 is a rear view of the apparatus shown in FIG. 1.

Inhaler retaining apparatus 14 includes a base 44 on which the inhaler 36 is placed and preferably secured since the base 44 is movable and rotatable. Actuating means, namely, an actuating device 46, is connected to the base 44 and arranged on the frame 20 to move the base 44 up and down in a vertical direction, guided by two or more vertical rods 48 (e.g., three as shown in FIGS. 2 and 4). In the lowermost position, the base 44 activates a weighing apparatus 50 to provide a measurement of the weight of the base 44, and through mathematical operations, the weight of the inhaler 36 on the base 44. Other structures for moving the base vertically is considered encompassed by actuating means.

A seal ring 52 is arranged on a front side of the base 44, and the base 44 is positioned relative to the carousel 12 to provide for a preferably air-tight seal between the seal ring 52 and the opening of one of the tubes 22 that engages with the inhaler 36 when pushed forward during the testing process.

Actuating device 16 is positioned on the other side of the base 44 from the carousel 12 so that the base 44 is between the actuating device 16 and the carousel 12. Actuating device 16 is a belt-driven drive screw 54 coupled to a motor and the drive screw 54 moves forward and backward, and when moving forward, it contacts the base 44. The drive screw 54 is capable of causing the inhaler 36 to move when retained on the base 44 between two positions, an upper position and a lower position (relative to the upper position). When the inhaler 36 is in the upper position, the forward movement of the drive screw 54 pushes against a part 56 of the base 44 on a side of the inhaler 36 and causes the inhaler 36 to rotate counterclockwise (when viewed from the front), with the rearward movement of the drive screw 54 causes the inhaler 36 to rotate clockwise back to its original position. Repeated forward and rearward movement of the drive screw 54 results in shaking of the inhaler 36.

When the inhaler 36 is in the lower position, the forward movement of the drive screw 54 pushes against the base 44 and causes the base 44 and inhaler 36 which is retained by the base 44 to move forward toward the carousel 12. There is a plate 58 alongside the carousel 12 and which includes an opening 60 (best seen in FIG. 6). An axial shaft 62 that passes through the carousel 12 is mounted onto the plate 58. When the inhaler 36 is moved forward as a result of the pushing by the drive screw 54, the seal ring 52 and a forward portion of the inhaler 36 moves through the opening 60 in the plate 58 until the seal ring 52 engages with the opening in the tube 22 aligning with the seal ring 52. Since the carousel 12 is rotatable, it is rotated until one of the tubes 22 is positioned properly to receive the seal ring 52 around the flange 30. The seal ring 52 thus ensures an air-tight seal between the space in the tube 22 and the outlet of the inhaler 36.

The carousel 12 can be rotated until all of the tubes 22 therein are sequentially positioned in the position to engage with the seal ring 52 and output of the inhaler 36. Rotation of the carousel 12 occurs when the base 44 is positioned so that the seal ring 52 is not in engagement with any of the tubes 22. Thus, the rotation of the carousel 12 is coordinated with the movement of the drive screw 54, which coordination can be achieved by a control unit 64 in housing 66 on the frame 20.

The second actuating device 18 includes an actuating rod 68 that moves out of and into a housing of the second actuating device 18. The actuating rod 68 is positioned so that its outward movement causes engagement with and depression of the canister 38 when the inhaler 36 is on the base 44. As mentioned above, this depression causes release of a metered dose of medicament from the valve stem through the nozzle orifice of the inhaler 36, and through the open end of the mouthpiece. The fast moving stream of atomized particles of the medicament passes through the seal ring 52 and the opening of the aligning tube 22 into the interior of the tube 22.

Actuating device 18 is also coupled to the control unit 64 in the housing 66 to enable the outward movement of the actuating rod 68 to be coordinated to the movement of the base 44 by actuating device 46 so that the actuating rod 68 is moved outward only when the base 44 is in the upper position and then has been moved forward by actuating device 16. The actuating device 18 may be controlled to maintain the actuating rod 68 in the outward position depressing the canister 38 for a predetermined amount of time.

A cover (not shown) is preferably provided over the carousel 12 to avoid inflow of airborne materials that may adversely affect the testing process. Similarly, the inhaler testing apparatus 10 also includes a cover over the lower part below the base 34, a cover over part of the actuating device 16, and a cover over a support for tubes when not in use. These covers may be transparent or opaque. The base 44 may also include apertures 72 for retaining tubes 22 when not in use (see FIG. 1).

Apparatus 10 may be used to test the inhaler 36 using any required delivery dose uniformity (DDU) testing protocol and for testing comparable inhalers and related devices.

One way to use apparatus 10 in an inhaler testing method, e.g., to make sure the inhaler 36 is providing the same dosage throughout its designed use, is to place the inhaler 36 to be tested on the base 44. Thirteen tubes 22 are placed onto the carousel 12, and the carousel 12 is rotated to an initial position in which a first one of the tubes 22 is in a position to receive the spray from the inhaler 36. The inhaler 36 is moved by the base 44 to the lowermost position in which it is weighed by weighing apparatus 50 to provide its initial weight. The base 44 is then moved upward by actuating device 46 along rod(s) 48 to a position in which the drive screw 54 will push the upper part of the inhaler 36 to shake it. The actuating device 16 is then actuated to cause the drive screw 54 to contact and shake the inhaler 36, which may occur one or more times.

The actuating device 16 is then controlled by control unit 64 to withdraw the drive screw 54 from contact with the inhaler 36 and out of the area of the base 44 to allow for continued upward movement of the base 44. Actuating device 46 then moves base 44 upward until the inhaler 36 is in a position in which the drive screw 54 will push the lower part of the inhaler 36 forward to press the seal ring 52 against the flange 30 of a first one of the tubes 22. The drive screw 54 is actuated by actuating device 16 to engage with and push the inhaler 36 forward until the seal ring 52 is around the flange 30 of the first tube 22.

The second actuating device 18 is then actuated to cause the actuating rod 68 to extend outward and engage with and depress the canister 38 for a set period of time (according to the testing protocol which is often 5 seconds) causing release of medicament from the inhaler 36 into the tube 22. The actuating device 18 is then actuated to cause the actuating rod 68 to move inward into its housing. Dosing of one dose into one of the tubes 22 is thus complete. The base 44 then is moved downward to be weighed by weighing apparatus 50, the carousel 12 is rotated by rotation mechanism 32 to position the next tube 22 in the position to receive a spray of medicament, and the process begins again.

When the inhaler 36 is designed for 100 sprays, the testing protocol may be to direct the first spray to waste and into one tube 22, collect and sample or test the next three sprays, designated sprays 2, 3 and 4 each in a respective tube 22, collect and sample or test the middle 4 sprays, designated sprays 48, 49, 50 and 51 each in a respective tube 22, and collect and sample or test the last three sprays, designated sprays 98, 99 and 100 each in a respective tube 22. Sprays designated 5-47 are also considered waste and sprayed into one tube 22, while sprays 52-97 are also waste and sprayed into another tube 22. The process is continued after spray 100 to empty the inhaler 36. Thus, a total of thirteen tubes 22 are needed for this testing protocol. For other, custom testing protocols, a different number of tubes 22 may be required and the carousel 12 is designed accordingly.

The testing process, including movement of the various actuating devices, may be controlled by a computer program in the control unit 64 in the housing 66. As noted above, the actuating devices may include one or more actuators and/or motors or any other comparable device that achieves the purpose(s) identified for the actuating device.

Figure 8:
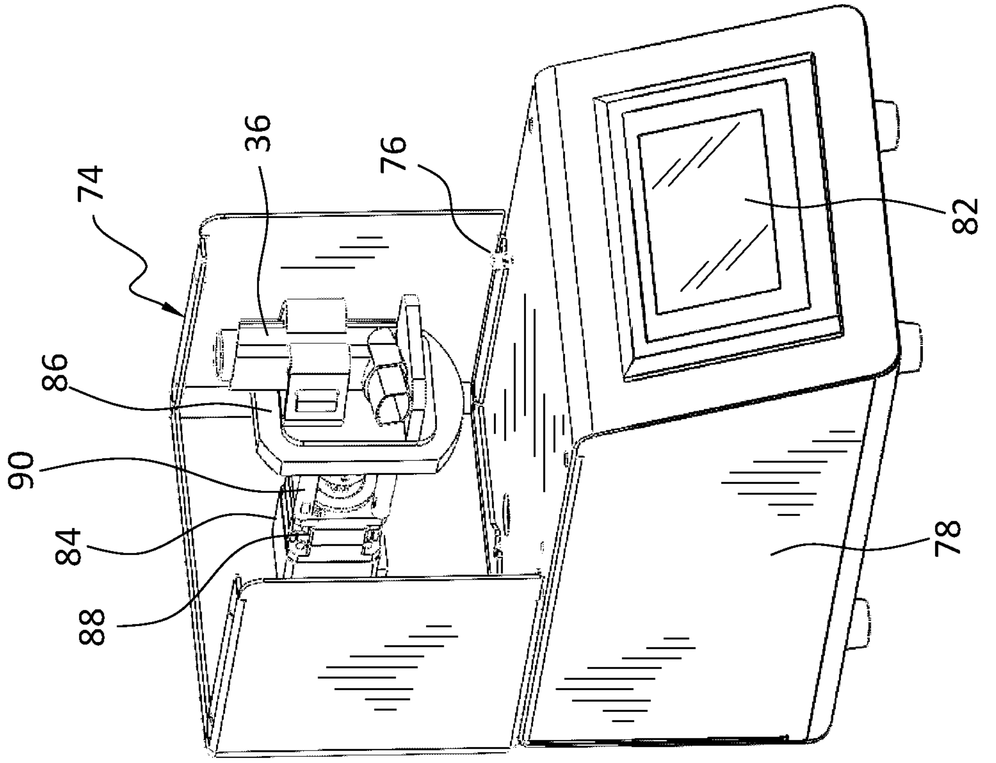
FIG. 8 is a view of the inhaler shaking apparatus shown in FIG. 7 with the cover removed.
Figure 7:
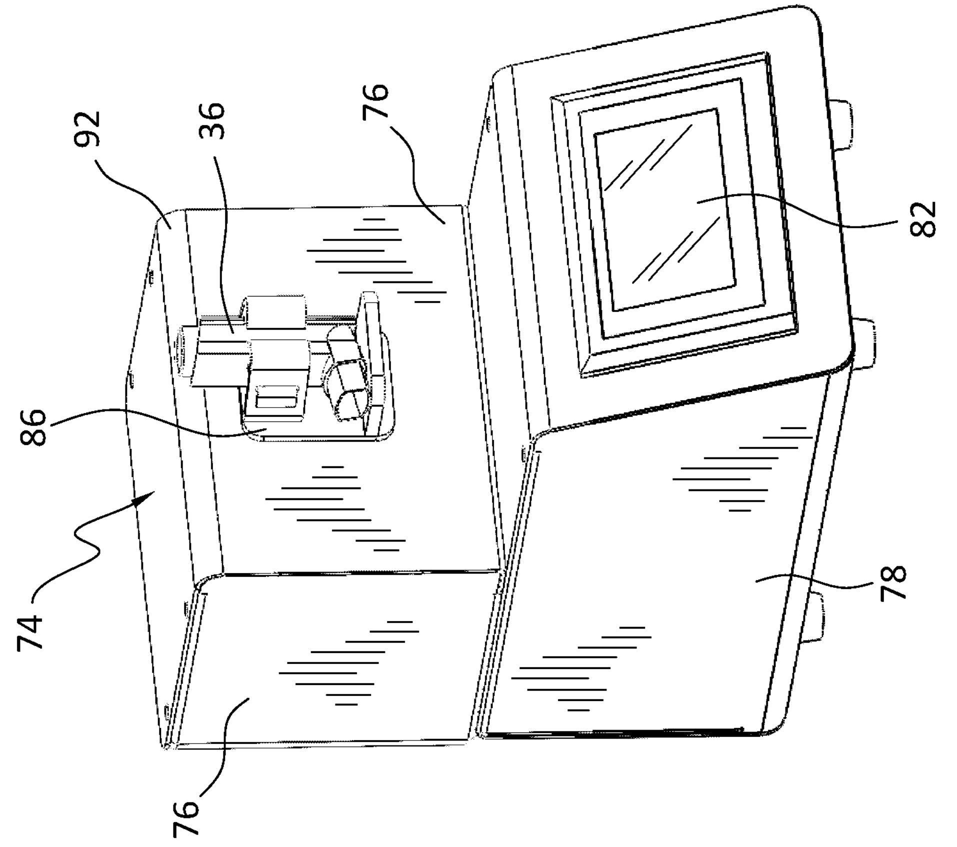
FIG. 7 is a perspective view of an inhaler shaking apparatus in accordance with the invention which may be used in combination with the apparatus shown in FIG. 1.
Figure 9:
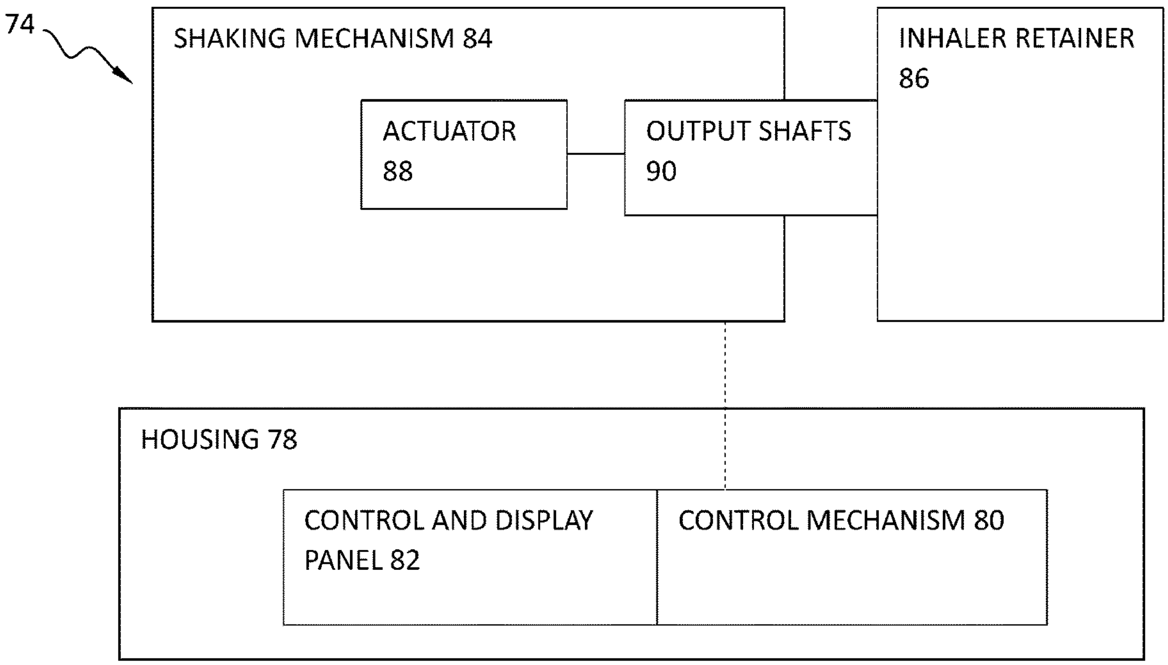
FIG. 9 is a schematic of the inhaler shaking apparatus of FIG. 7.

Referring now to FIGS. 7-9, an inhaler shaking apparatus 74 in accordance with the invention is designed to address the issue that during inhaler testing, pharmaceutical scientists need to shake the formulation with at least a few shakes to get the maximum drug spray out the inhaler canister, but in the research and development stage, do not know what the right formulation is. In order to let the patients just shake few times to get all the drugs in an inhaler, inhaler shaking apparatus 74 may be used to test and improve the formulation. Inhaler shaking for inhaler testing purposes is typically done manually, and hence inhaler shaking apparatus 74 provides a significant improvement by making this shaking automated and thus considerably easier.

Inhaler shaking apparatus 74 includes a frame 76 defining a housing 78 in a lower part for housing a control mechanism 80 (a controller which may include a processor and associated electronic components such as programmable logic controller, PLC), see FIG. 9 in which it is shown schematically. Control and display panel 82 is arranged on an exterior of the housing 78, coupled to the control mechanism 80, and may be a touch screen. Shaking mechanism 84 is above the housing 78 and controlled by the control mechanism 80 which in turn may be programmed by a user manipulating the control and display panel 82. Control and display panel 82 also shows operating parameters of the apparatus 74.

Control mechanism 80 and control and display panel 82 may be integrated into a common component, which may be referred to as control means for controlling the shaking mechanism 84. These control means may be structure known to those skilled in the art to allow for programming of a processor to cause operation of a motor in accordance with the programming.

Shaking mechanism 84 is attached to an inhaler retainer 86 which is configured to securely retain an inhaler 36 which is sought to be shaken. Shaking mechanism 84 comprises an actuator 88 such as a step motor that has one or more output shafts 90 that are rotated upon actuation of the step motor thereby causing the inhaler retainer 86 to rotate, and shaking of the inhaler 36 when secured by the inhaler retainer 86. A cover 92 may be provided to cover the actuator 88 and output shafts 90. FIG. 9 is a schematic of the shaking apparatus 74.

The degree of rotation may be a 180 degree turn, i.e., from the vertical state shown in FIGS. 7 and 8 (a first orientation of the inhaler 36) to a completely upside down state (a second, different orientation of the inhaler 36), and this rotation is repeated as per the programming entered into the control means by manual use of the control and display panel 82. The inhaler 36 is therefore rotated in a series of 180 degree turns about an axis of rotation that may be defined by the output shaft 90 in order to obtain a shaking effect. The rotation of the inhaler retainer 86 and inhaler 36 secured thereto causes shaking of the contents of the canister 38 in the inhaler 36.

Inhaler 36 may be secured to the apparatus 74 when it is sought to be shaken in conjunction with the testing being performed by the inhaler testing apparatus 10, in particular, prior to the start of the test.

Figure 12:
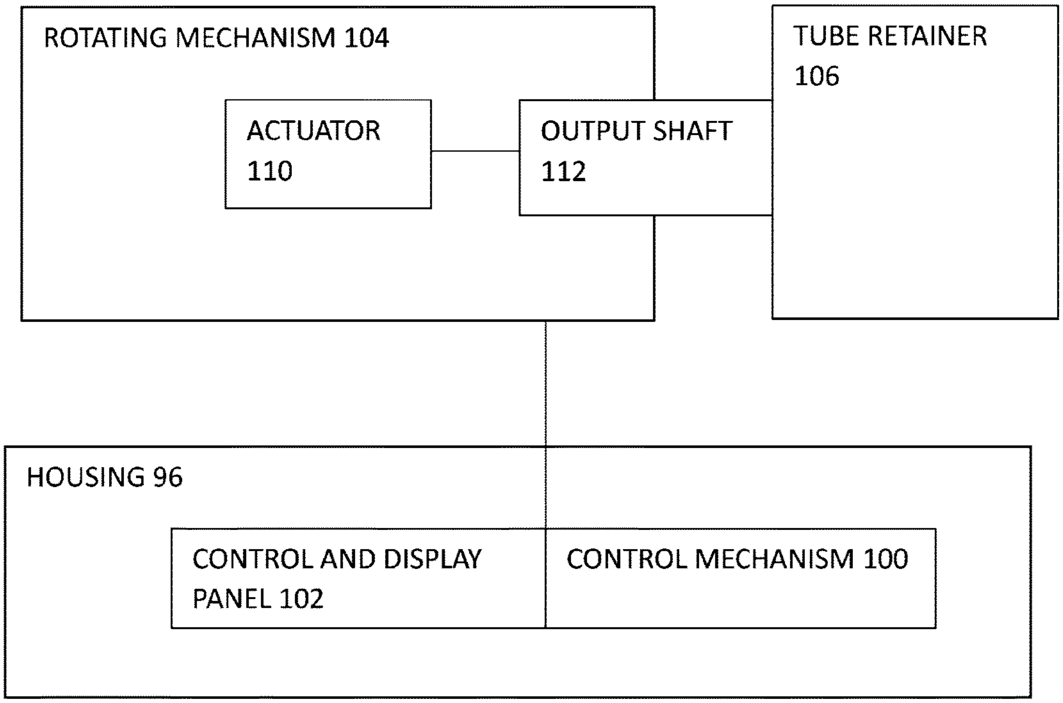
FIG. 12 is a schematic of the tube washing device of FIG. 10.
Figure 11:
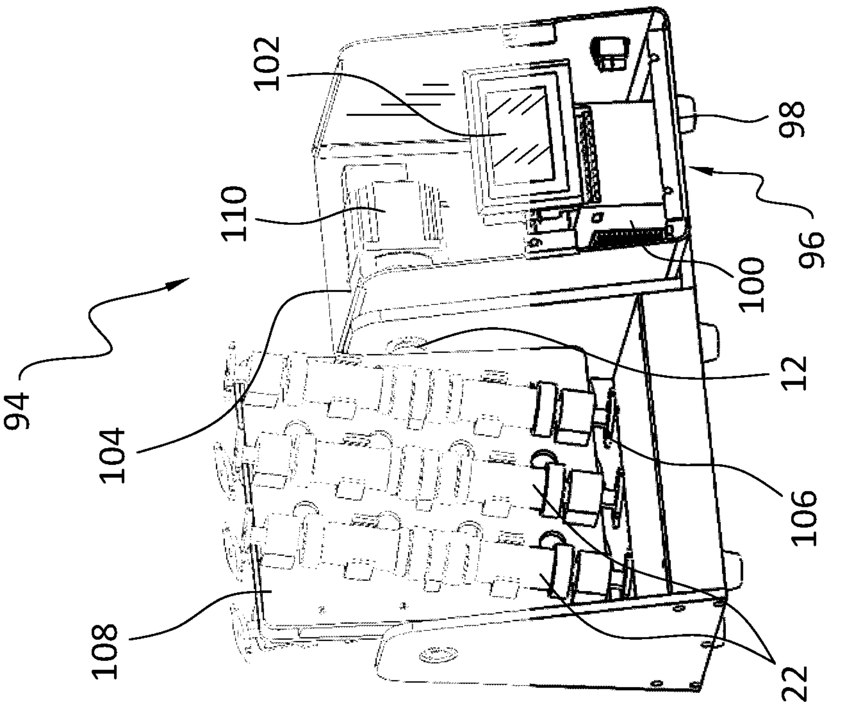
FIG. 11 is a view of the tube washing device shown in FIG. 10 with the cover removed.
Figure 10:
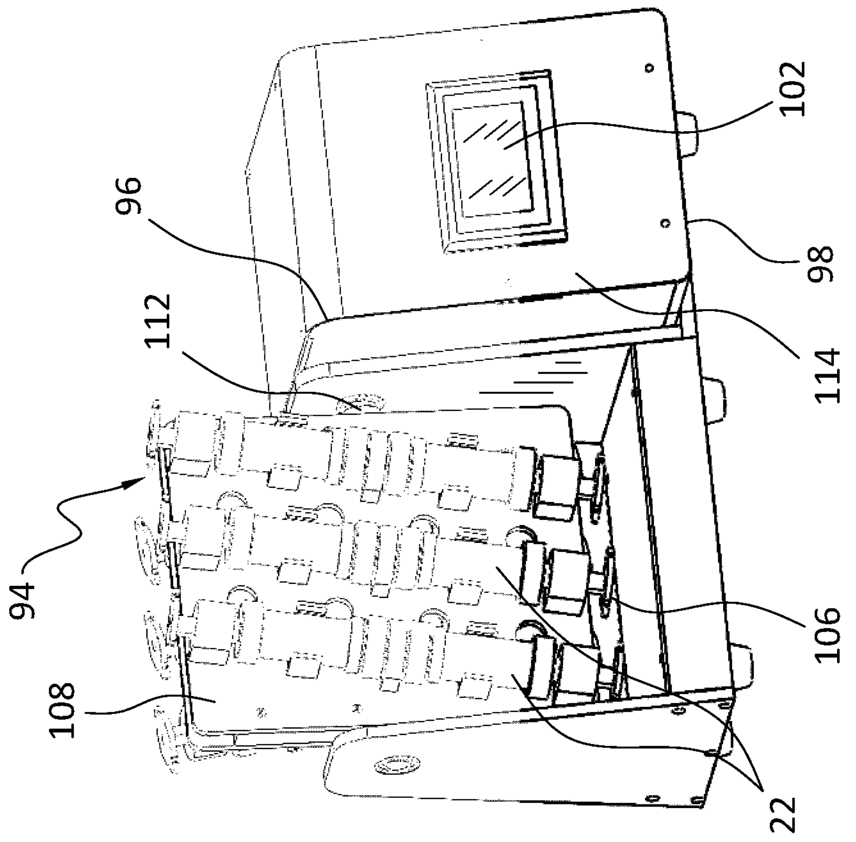
FIG. 10 is a perspective view of a tube washing device in accordance with the invention which may be used in combination with the apparatus shown in FIG. 1.

Referring now to FIGS. 10-12, a washing device 94 in accordance with the invention is designed to wash out, in each of a plurality of sample tubes, the sample from the test and solution in the sample tubes. In prior art inhaler testing processes, DDU tubes were washed manually, and the user had to put the solution into a syringe and wash the DDU tube stoke by stoke. Washing device 94 is designed to address this problem and provide for automated washing of DDU tubes, notably after use of inhaler testing apparatus 10 to test inhalers.

Inhaler testing apparatus 10 uses a plurality of sample tubes 22, also referred to as DDU tubes. These tubes 22 receive the sprayed inhaler medicament being injected from the inhaler 36 during a test. The pharmaceutical scientists manually put solvent (solution) into each sample tube, and shake it to make the sample received during the test dissolve in the solution and then take the solution for analysis. Thereafter, all the washing of the DDU tubes 22 for subsequent use in prior art inhaler testing is done by hand. Washing device 94 addresses this issue and provides for automated or automatic washing of the tubes 22 after the test using inhaler testing apparatus 10. The intended use of the device 94 identified herein is not critical to the invention.

Washing device 94 includes a frame 96 defining a housing 98 on one side for housing a control mechanism 100 (processor and associated electronic components such as programmable logic controller, PLC), see FIG. 12 in which it is shown schematically. A control and display panel 102 is arranged on an exterior of the housing 98, coupled to the control mechanism 100 and may be a touch screen. A rotation mechanism 104 is partly in the housing 98 and controlled by the control mechanism 100 which in turn may be programmed by a user manipulating the control and display panel 102. Control and display panel 102 also shows operating parameters of the apparatus 94.

The control mechanism 100 and control and display panel 102 may be integrated into a common component, which may be referred to as control means for controlling the rotation mechanism 104. These control means may be structure known to those skilled in the art to allow for programming of a processor to cause operation of a motor in accordance with the programming.

Rotation mechanism 104 is attached to a tube retainer 106 which is configured to securely retain a plurality of tubes 22 (twelve as illustrated with six on each side of a support plate 108) which are sought to be washed. Two tubes 22 are longitudinally oriented to form three rows or tubes with two tubes end-to-end in each row on each side of the support plate 108. There is a mechanism to removably secure each of the tubes 22 to the support plate 108.

The rotation mechanism 104 comprises an actuator 110 such as a step motor that has a horizontal output shaft 112 extending partly outside of the housing 98 and that is rotated upon actuation of the step motor thereby causing the tube retainer 106 to rotate, and mixing of the tubes 22 when secured by the tube retainer 106. Mixing of the tubes 22, when having a washing solution therein, serves to wash the tubes 22. A cover 114 may be provided to cover the actuator 110 and output shaft 112.

FIG. 12 is a schematic of the washing apparatus 94.

The degree of rotation of the tube retainer 106 may be a full 360 degree turn, and involve several complete revolutions about an axis defined by the output shaft 112. The number of revolutions is determined as per the programming entered into the control means by manual use of the control and display panel 102. The rotation of the tube retainer 106 and tubes 22 secured thereto causes mixing of the contents of the tubes 22.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention. All of the prior art identified above is incorporated by reference herein. The apparatus is not required to include tubes and may be considered an invention without inclusion of the tubes, although the tubes are needed for inhaler testing. Other structures, such as the covers, is also not essential to the invention, although preferred at times.

The invention claimed is:

1. An inhaler testing apparatus, comprising:

a frame;

a rotatable carousel rotatably mounted on said frame and configured to support a plurality of tubes each having a closed end and an open end, an inhaler retaining apparatus on said frame and configured to retain an inhaler;

first actuating means on said frame for moving said inhaler retaining apparatus along a first axis;

second actuating means on said frame for shaking the inhaler when retained by said inhaler retaining apparatus and moving said inhaler retaining apparatus along a second axis;

third actuating means on said frame for engaging with and actuating the inhaler when retained by said inhaler retaining apparatus; and a control unit on said frame that controls said carousel, said first actuating means, said second actuating means and said third actuating means to move said carousal relative to the inhaler when retained by said inhaler retaining apparatus to cause controlled shaking of the inhaler and delivery of material from the inhaler into each of the tubes when supported by said carousel, whereby analysis of the material in the tubes constitutes a test of the inhaler.

2. The apparatus of claim 1, wherein said carousel comprises at least one plate having a plurality of openings, each of said openings being configured to support a respective one of the tubes.

3. The apparatus of claim 1, further comprising a rotation mechanism attached to said carousel for rotating said carousel about a horizontal, central axis, said rotation mechanism including a motor underneath a base, said carousel being above said base.

4. The apparatus of claim 1, wherein said inhaler retaining apparatus comprises a base for supporting the inhaler, said first actuating means being configured to move said base vertically between uppermost and lowermost positions.

5. The apparatus of claim 4, further comprising a weighing apparatus for obtaining a weight of the inhaler when retained by said inhaler retaining apparatus and when said base is in the lowermost position.

6. The apparatus of claim 4, wherein said second actuating means comprise a movable drive screw that engages with the inhaler when retained by said inhaler retaining apparatus and when moved alternatingly in first and second opposite directions causes shaking of the inhaler when supported on said base.

7. The apparatus of claim 6, wherein said drive screw is also configured to engage with said base and move the inhaler when retained by said inhaler retaining apparatus toward and away from a respective one of the tubes when supported by said carousel.

8. The apparatus of claim 7, wherein said third actuating means are configured to press a canister of the inhaler when retained by said inhaler retaining apparatus and having an outlet in sealed communications with the respective one of the tubes to cause delivery of material from the inhaler into the respective tube.

9. The assembly of claim 8, wherein said third actuating means comprise an actuating rod that is movable in opposite directions.

10. An inhaler testing method, comprising:

placing a plurality of tubes in a rotatable carousel rotatably mounted on a frame, each of the tubes having a closed end and an open end;

placing the inhaler on an inhaler retaining apparatus on the frame;

controlling movement of the inhaler retaining apparatus along a first axis and a second axis relative to rotation of the carousel and activation of the inhaler to cause controlled shaking of the inhaler and delivery of material from the inhaler into each of the tubes; and analyzing the material in the tubes.

11. The method of claim 10, further comprising rotating the carousel such that each of the tubes receives a respective one of a plurality of deliveries of material from the inhaler.

12. The method of claim 10, further comprising weighing the inhaler between each delivery of material from the inhaler to each of the tubes.

13. The method of claim 10, further comprising providing a common actuating mechanism to move the inhaler against each of the tubes and to shake the inhaler prior to movement against each of the tubes.

14. The method of claim 10, wherein the step of controlling movement of the inhaler retaining apparatus along the first axis and the second axis relative to rotation of the carousel and activation of the inhaler to cause controlled shaking of the inhaler and delivery of material from the inhaler into each of the tubes comprises selecting specific doses of a total amount of doses provided by the inhaler for testing and wasting other doses.

* * * * *